United States Patent [19]

Segal

[11] Patent Number: 4,754,675
[45] Date of Patent: Jul. 5, 1988

[54] TISSUE SLICING DEVICE

[76] Inventor: Joseph Segal, 4 Boodenheimer Street, Kiryat Hayovel, Jerusalem 96551, Israel

[21] Appl. No.: 940,916

[22] Filed: Dec. 12, 1986

[30] Foreign Application Priority Data

Oct. 8, 1986 [IL] Israel .......................... 79061

[51] Int. Cl.⁴ .................................... G01N 1/06
[52] U.S. Cl. .................................... 83/437; 83/464; 83/467 R; 83/761; 83/915.5
[58] Field of Search .................. 83/437, 462, 463, 464, 83/465, 466, 761, 762, 763, 467 R, 651.1, 915.5; 30/124

[56] References Cited

U.S. PATENT DOCUMENTS 1,265,232  5/1918  Miller ........................ 83/437
3,965,573  6/1976  Mims ......................... 83/764 X Primary Examiner—E. R. Kazenske
Assistant Examiner—Hien H. Phan

[57] ABSTRACT

A tissue slicing device is provided comprising of stationary floor, side wall and back wall; a movable L-shaped side wall, a sliding-removable front wall; a telescopically adjusted and movable cross bar stationed between and atop the said walls and floor, respectively, whose movement is governed by a millimetrically regulated apparatus, and an L-shaped cover moving above and aside said holder and its stationary side wall, respectively, whose movement is governed by a millimetrically regulated apparatus. A fixed gap is situated between the said two side wall and front wall, on top of which the said L-shaped cover is guided to form a slit of a desirable size, consistent with the thickness of the tissue slice to be prepared, through and along which an excising knife is passed.

1 Claim, 1 Drawing Sheet

TISSUE SLICING DEVICE

This invention is related to a device serving as a means for the preparation of fresh tissue slices, obtained primarily from small laboratory animals such as rodents and the like, suitable for metabolic studies. There are several types of devices which are currently used to prepare tissue slices. Some devices, microtomes, are used in the preparation of slices, 1 micrometer thick and the like, as described in U.S. Pat. No. 3,286,575, U.S. Pat. No. 3,613,492. Others are employed to obtain slices 0.5 millimeter thick and the like as described by William C. Stadie and Benjamin C. Riggs in The Journal of Biological Chemistry, Volume 154, pages 687–690, 1944; currently manufactured by Arthur H. Thomas Company, Philadelphia, Pa., U.S.A.

However, the micrometer-thick slices prepared by means of a microtome are not fresh, too fragile, and are not suitable for the metabolic studies referred hereinabove, while the said Stadie-Riggs apparatus, although more suitable for the said purpose, suffers from several drawbacks; the major drawback is its lack of preciseness, concerning the thickness of the prepared slice, which is an absolute requirement for the said metabolic studies, and hence the reproducibility of uniformly excised slices is poor, and its reliability is therefore questionable. In addition, the operation of the said Stadie-Riggs apparatus is quite sluggish.

SUMMARY OF THE INVENTION

Therefore, it is the primary object of this invention to provide a means for the preparation of fresh tissue slices having a precise and uniform thickness ranging between 0.2 and 20 millimeter in size. The other advantages of this invention is that it is cost efficient, easy to operate, and that the tissue slices are prepared quickly and with high reproducibility.

Briefly, the tissue slicing device is comprised of a holder for the specimen to be sliced and an excising knife having a 0.1 millimeter thick blade. The said holder is made of a transparent solid plastic material, such as plexiglass or perpex, and consists of a stationary floor, stationary back wall, and a stationary side wall adhere to one another; a removable, upwards-sliding, front wall; a transversly movable L-shaped side wall; a telescopically adjusted cross bar, positioned atop and between the said floor and the said side walls of said holder, respectively, mounted with a millimetric screw governing its movement atop and between the said floor and side walls of said holder, respectively; and an L-shaped cover anchored to and sliding above and aside said stationary side wall mounted with a millimetric screw governing its movements atop and aside the said holder and its stationary side wall, respectively. The specimen, which is introduced into the said holder through the front openning while the front wall is away, is arrested by means of the said movable side wall and cross bar, and is guided by the cross bar, whose movement is governed by the said millimetric screw, onto the fixed gap positioned between the said side walls and the front wall, and secured tightly against the said front wall. The said L-shaped cover is then precisely adjusted above said specimen so to fashion a slit, matching the desirable slice thickness, along which the said excising knife is guided down and through the said specimen to form the tissue slice.

BRIEF DESCRIPTION OF THE DRAWINGS

FIG. 1 is a top view and FIG. 2 is a front view of the said device.

DETAILED DESCRIPTION OF THE REFERRED EMBODIMENT

Figure 1:
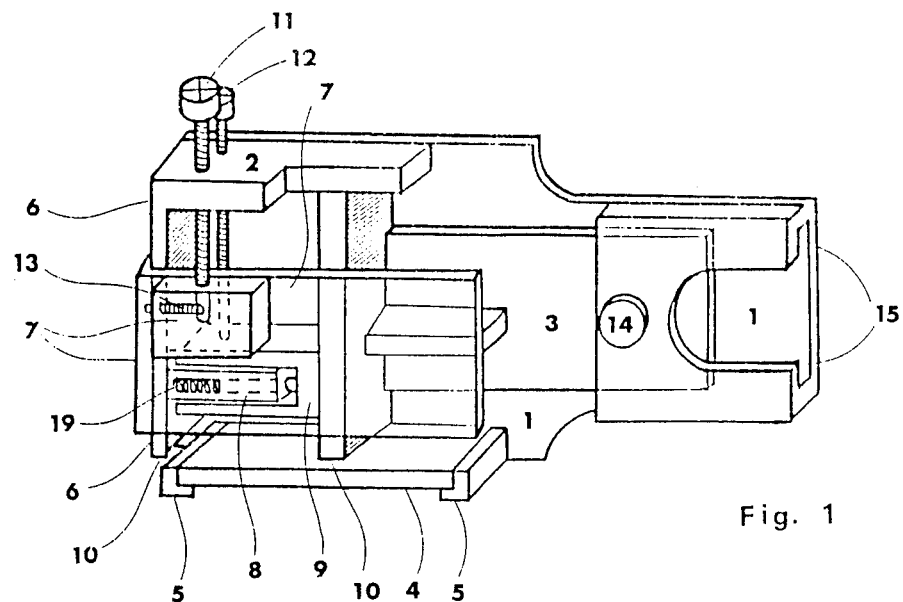
FIGS. 1 and 2 are a perspective view of the tissue slicing device, where
Figure 2:
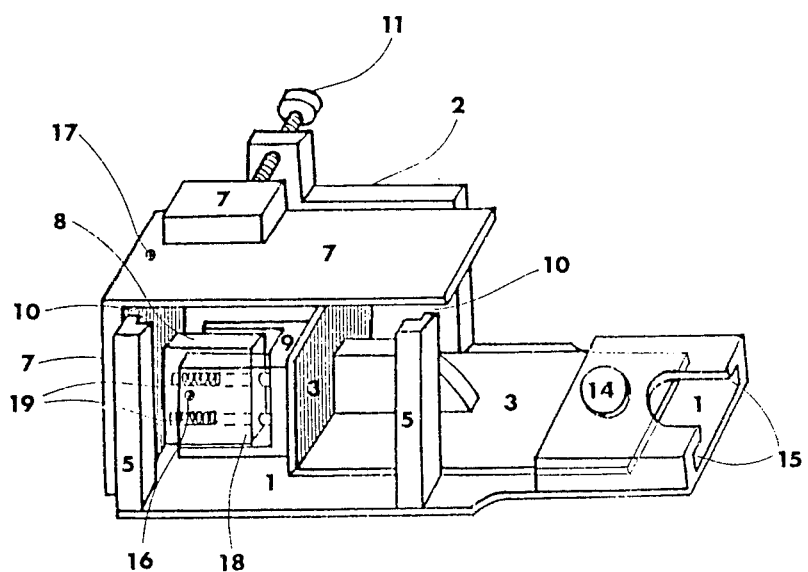

The tissue slicing device is comprised of a holder in which the specimen to be sliced is placed, which is to be described hereinafter, and an excising knife having a 0.1 millimeter thick blade, which is well defined and known to those having skill in the art.

Referring now to the drawings, the said holder, which is made of a transparent plastic material, such as plexiglass or perpex; however, it should be realized that materials other than those specified herein having comparable properties could also be used, is comprised of a floor 1, shaped as shown or in straight border-line; a stationary back wall 2 and a stationary side wall 6 adhere to said floor; an L-shaped movable side wall 3, whose movement towards and away from the said stationary side wall is guided by paths 15, and which can be affixed to said floor by screw 14; a removable front wall 4 sliding in and out of position along supporting paths 5; and an L-shaped cover 7, anchored to and sliding above and aside the said stationary side wall by means of a guiding screw 17 (another such guiding screw can be stationed at the lower section of the descending part of the said L-shaped cover to provide a firmer anchorage), and whose movement towards and away from the said front wall is governed by a millimetric screw 11, which is secured to said L-shaped cover by screw 13. The said holder also consists of a telescopically adjusted and movable cross bar 18, consisting of a part 8 equipped with two springs 19, which moves in and out of a U-shaped part 9 equipped with two pins which lie inside the housing of and against the said springs to provide the said cross bar with its telescopic adjustability. The two said parts of the said cross bar are held together by means of a screw 16. The movement of the said cross bar towards and away from the said front wall is governed by a millimetric screw 12, which is secured to said cross bar by a screw (not shown) similar to screw 13. The elements of said holder described herein are all known to those having skill in the art.

The procedure involved in the preparation of a tissue slice is as follows: The front wall 4 is removed, the specimen to be sliced is introduced into the said holder and placed on floor 1, being so enclosed by the two side walls 3 and 6 and the cross bar 18, and the said front wall is then slided back in place. The said specimen is first secured against the stationary side wall 6 by sliding side wall 3 towards said stationary side wall, which is then secured to said floor by screw 14. Then, the said specimen is guided towards and arrested against the front wall 4 by the cross bar 18 whose movement is guided by the millimetric screw 12. By now, the said specimen is enclosed and firmly secured by the two said side walls, the said front wall, and the said cross bar. The L-shaped cover 7 is then guided by the millimetric screw 11 towards the front wall, about and above the narrow fixed gap 10 stationed between the two said side walls and the said front wall, so to fashion a slit of a precise size, matching the desirable thickness of the tissue slice to be prepared. The said knife is then introduced through the said slit and is lowered down and through the said specimen with a to and fro motion, while being supported against and guided by the descending part of the said L-shaped cover, until slicing is completed. The front wall is then lifted up and away, and the slice formed is transferred away. The front wall is then placed back, the remaining specimen is rearrested against the front wall and the side walls and a second slice is prepared.

What is claimed is:

1. A tissue slicing device for the preparation of fresh tissue slices for metabolic studies comprising of a holder consisting of a stationary floor; a stationary side wall; a stationary back wall; a slide-removable front wall; a tranversly movable L-shaped side wall; a telescopically adjusted and movable cross bar, stationed between and atop the said side walls and floor, respectively, mounted with a millimetrically regulated apparatus governing its movement atop and along the said stationary floor and side walls of said holder, respectively, so to adjust and secure about specimen in said holder and to feed said specimen onto a fixed slit situated between the said side walls and the said front wall; and a sliding L-shaped cover, anchored onto the said stationary side wall, mounted with a millimetrically regulated apparatus governing its movement, towards and away from said front wall, atop and aside the said holder and its stationary side wall, respectively, so to fashion a desirable section-slit, bordered by the said front wall, guiding an excising knife.

* * * * *